(12) United States Patent
Yang et al.

(10) Patent No.: US 10,183,984 B2
(45) Date of Patent: *Jan. 22, 2019

(54) METHOD FOR EXTRACTING RECOMBINANT HUMAN SERUM ALBUMIN FROM TRANSGENIC RICE GRAIN

(71) Applicant: Healthgen Biotechnology Corp., Wuhan (CN)

(72) Inventors: Daichang Yang, Wuhan (CN); Yang He, Wuhan (CN); Guangfei Li, Wuhan (CN)

(73) Assignee: Healthgen Biotechnology Corp., Wuhan, Hubei (CN)

( * ) Notice: Subject to any disclaimer, the term of this patent is extended or adjusted under 35 U.S.C. 154(b) by 157 days.

This patent is subject to a terminal disclaimer.

(21) Appl. No.: 14/996,092

(22) Filed: Jan. 14, 2016

(65) Prior Publication Data

US 2016/0122414 A1    May 5, 2016

Related U.S. Application Data

(63) Continuation of application No. 13/206,844, filed on Aug. 10, 2011, now Pat. No. 9,255,138.

(30) Foreign Application Priority Data

Dec. 20, 2010  (CN) .......................... 2010 1 0597544

(51) Int. Cl.
*C07K 1/14* (2006.01)
*C07K 14/765* (2006.01)

(52) U.S. Cl.
CPC .................................. *C07K 14/765* (2013.01)

(58) Field of Classification Search
None
See application file for complete search history.

(56) References Cited

U.S. PATENT DOCUMENTS

| | | | |
|---|---|---|---|
| 2,705,230 A | 3/1955 | Reid | |
| 4,446,163 A | 5/1984 | Galle et al. | |
| 4,754,019 A | 6/1988 | Gion et al. | |
| 5,459,048 A | 10/1995 | Kuner et al. | |
| 5,521,287 A * | 5/1996 | Ohmura | C07K 14/765 530/363 |
| 5,561,115 A | 10/1996 | Tenold | |
| 5,612,196 A | 3/1997 | Becquart | |
| 7,193,041 B2 | 3/2007 | Perry et al. | |
| 7,304,208 B2 | 12/2007 | Rodriquez et al. | |
| 7,423,124 B2 | 9/2008 | Belew | |
| 8,058,407 B2 | 11/2011 | Sun et al. | |
| 9,023,990 B2 | 5/2015 | Yang et al. | |
| 9,951,100 B2 | 4/2018 | Yang et al. | |
| 2001/0034053 A1 | 10/2001 | Winge | |
| 2002/0127661 A1 | 9/2002 | Farwick | |
| 2003/0170810 A1 | 9/2003 | Vedadi et al. | |
| 2005/0214902 A1 | 9/2005 | Belew | |
| 2007/0293420 A1 | 12/2007 | Schumann et al. | |
| 2008/0206436 A1 | 8/2008 | Strohbehn et al. | |
| 2008/0318277 A1 | 12/2008 | Huang et al. | |
| 2009/0105465 A1 | 4/2009 | Arunakumari et al. | |
| 2010/0031394 A1 | 2/2010 | Huang et al. | |
| 2010/0047428 A1 | 2/2010 | Lejars et al. | |
| 2010/0190708 A1 | 7/2010 | Tsuno et al. | |
| 2012/0315697 A1 * | 12/2012 | Pettit | C07K 14/76 435/326 |
| 2015/0203530 A1 | 7/2015 | Yang et al. | |
| 2015/0329618 A1 | 11/2015 | Yang et al. | |

FOREIGN PATENT DOCUMENTS

| | | |
|---|---|---|
| CN | 1896239 | 1/2007 |
| CN | 100540667 | 9/2009 |
| CN | 101665798 | 3/2010 |
| CN | 101768206 | 7/2010 |

(Continued)

OTHER PUBLICATIONS

Belew et al., "Purification of recombinant human serum albumin (rHSA) produced by genetically modified Pichia Pastoris," Separ Sci Tech (2008) 43:3134-3153.
Bio-Rad BioProcess International (2010), http://www.bioprocessintl.com/journal/2010/July_August/Nuvia-S-Media, retreived from Internet May 10, 2013, 4 pages.
Cabrera-Crespo et al., "Albumin purification from human placenta," Biotechnol Appl Biochem (2000) 31:101-106.
Chen et al., "Purification of recombinant human serum albumin from fermentation broth," Pharm Biotechnol (2003) 10(1):25-27 (English language abstract).
Chinese Application No. CN-200510019084.4, filed Jul. 13, 2005, 31 pages.
Englard et al., "Precipitation Techniques," Method in Enzymology (1990) 182:285-300.
Hegyi et al., Introduction to Practical Biochemistry (2013), pp. 1-2, 89-104.

(Continued)

*Primary Examiner* — Marsha Tsay
(74) *Attorney, Agent, or Firm* — Rimon, P.C.

(57) ABSTRACT

A method for extracting recombinant human serum albumin (rHSA) from transgenic rice grain is provided, comprising the steps of: 1) grinding dehusked rice containing rHSA into milled rice grain with a fineness of 80~120 mesh, which is mixed with a extraction buffer in a w/v ratio of 1:5, then extracting at 55~60° C. for 1~3 hours to obtain mixture I; said extraction buffer comprises 10~30 mM phosphate buffer, 10~20 mM sodium acetate, 15~30 mM ammonium sulfate and 5~20 mM sodium caprylate and has a pH of 6.5~8; 2) adjusting the pH of mixture I to 4.0~4.5, followed by precipitating at room temperature for 3~12 hours to obtain mixture II; 3) filtering the mixture II and collecting the filtrate, to obtain a solution containing high concentration of rHSA. The concentration of rHSA in the resultant solution is 650~660 µg/mL, which increases by 1.15 times comparing to the extraction amount before improvement, and the amount of non-target protein is reduced by 2.46 times. The method provides a basis for subsequent purification of rHSA.

20 Claims, 6 Drawing Sheets

(56) References Cited

FOREIGN PATENT DOCUMENTS

| CN | 102127164 | 7/2011 |
|---|---|---|
| CN | 102190722 | 9/2011 |
| CN | 102532254 | 7/2012 |
| EP | 0428758 | 5/1991 |
| EP | 0683233 | 5/1995 |
| WO | WO-90/15617 | 12/1990 |
| WO | WO-2000/044772 | 8/2000 |
| WO | WO-2004/099405 | 11/2004 |
| WO | WO-2012/083580 | 6/2012 |

OTHER PUBLICATIONS

Huang et al., "Production of human serum albumin by sugar starvation induced promoter and rice cell culture," Transgenic Res (2005) 14(5):569-581.
Latta et al., "Synthesis and purification of mature human serum albumin from E. coli," Biotechnology (1987) 5:1309-1314.
Macro-Prep® HIC Support product information, 2 pages.
Mavituna "Production of recombinant human serum albumin in transgenic plants and plant cells," Dissertation, Doktorin der Naturwissenschaften (2005), pp. 1-143.
SAFC Biosciences, "Protein Purification Techniques," (2006) 1:1-2.
Saunders et al., "Secretion of human serum albumin from Baillus subtilis," J. of Bateriology (1987) 169(7):2917-2925.
Office Action for U.S. Appl. No. 13/206,844, dated Jul. 16, 2013, 9 pages.
Response to Office Action for U.S. Appl. No. 13/206,844, dated Oct. 16, 2013, 7 pages.
Final Office Action for U.S. Appl. No. 13/206,844, dated Dec. 27, 2013, 17 pages.
Request for Continued Examination in U.S. Appl. No. 13/206,844, filed Apr. 28, 2014, 13 pages.
Office Action for U.S. Appl. No. 13/206,844, dated Aug. 27, 2014, 20 pages.
Response to Office Action for U.S. Appl. No. 13/206,844, dated Feb. 26, 2015, 15 pages.
Office Action for U.S. Appl. No. 13/206,844, dated Jun. 4, 2015, 18 pages.
Response to Office Action for U.S. Appl. No. 13/206,844, filed Sep. 4, 2015, 6 pages.
Notice of Allowance for U.S. Appl. No. 13/206,844, dated Oct. 1, 2015, 7 pages.
Office Action for U.S. Appl. No. 13/206,884, dated May 22, 2013, 19 pages.
Response to Office Action in U.S. Appl. No. 13/206,884, filed Aug. 22, 2013, 26 pages.
Final Office Action for U.S. Appl. No. 13/206,884, dated Oct. 25, 2013, 25 pages.
Response to Final Office Action for U.S. Appl. No. 13/206,884, filed Jan. 27, 2014, 24 pages.
Advisory Action for U.S. Appl. No. 13/206,884, dated Feb. 25, 2014, 4 pages.
Request for Continued Examination in U.S. Appl. No. 13/206,884, filed Apr. 25, 2014, 42 pages.
Notice of Allowance for U.S. Appl. No. 13/206,884, dated Jan. 2, 2015, 10 pages.
Issue Fee Payment for U.S. Appl. No. 13/206,884, filed Apr. 1, 2015, 3 pages.
Non-final Rejection for U.S. Appl. No. 14/676,727, dated Aug. 1, 2016, 19 pages.
Response to Non-final Rejection for U.S. Appl. No. 14/676,727, dated Jan. 31, 2017, 29 pages.
Final Rejection for U.S. Appl. No. 14/676,727, dated May 24, 2017, 32 pages.
Response to Final Rejection for U.S. Appl. No. 14/676,727, dated Aug. 9, 2017, 32 pages.
Advisory Action for U.S. Appl. No. 14/676,727, dated Sep. 8, 2017, 4 pages.
Notice of Appeal filed for U.S. Appl. No. 14/676,727, dated Nov. 22, 2017, 7 pages.
Pre-Brief Appeal Conference Decision for U.S. Appl. No. 14/676,727, dated Dec. 6, 2017, 2 pages.
Notice of Allowance for U.S. Appl. No. 14/676,727, dated Jan. 10, 2018, 7 pages.
He et al., "Large-scale production of functional human serum albumin from transgenic rice seeds," PNASA (2011) 108(47):19078-19083.
GE Healthcare, "Instructions 11-0035-05 AA," Capto MMC (2005) 24 pages.
Lees et al., "Purifiying a recalcitrant therapeutic recombinant protein with a mixed-mode chromatography sorbent," BioProcess International (2009) 42-48.
Non-final Rejection for U.S. Appl. No. 14/653,258, dated Jun. 27, 2017, 15 pages.
Response to Non-final Rejection for U.S. Appl. No. 14/653,258, dated Sep. 27, 2017, 15 pages.
Final Rejection for U.S. Appl. No. 14/653,258, dated Nov. 15, 2017, 18 pages.
International Preliminary Report on Patentability for PCT/CN2013/075405, dated Apr. 13, 2015, 15 pages (Including English Translation).
International Search Report for PCT/CN2013/075405, dated Sep. 26, 2013, 7 pages (Including English Translation).
USPTO, Non-Final Office Action for U.S. Appl. No. 15/917,529, dated Jun. 7, 2018, 21 pages.

* cited by examiner

Fig. 10

METHOD FOR EXTRACTING RECOMBINANT HUMAN SERUM ALBUMIN FROM TRANSGENIC RICE GRAIN

CROSS-REFERENCE TO RELATED APPLICATIONS

This is a continuation application of co-pending U.S. patent application Ser. No. 13/206,844, filed Aug. 10, 2011, now allowed, which claims the priority of Chinese Application No. 201010597544.2, filed on Dec. 20, 2010. The entire contents of these prior applications are incorporated herein by this reference.

FIELD OF THE INVENTION

The present invention relates to the field of biotechnology, and more particularly to a method for extracting recombinant human serum albumin (rHSA) from transgenic rice grain.

BACKGROUND OF THE INVENTION

Human serum albumin (HSA) is a single chain, non-glycosylated protein consisting of 585 amino acids, having a molecular weight of 66.5 kD and an isoelectric point between 4.7~4.9. It is the most abundant protein in human blood plasma, making up about 60% of the total plasma proteins. There is about 40 g of HSA in per liter of human blood. Besides being present in the plasma, HSA is also found in tissues and body secretions, skins and lymph cavities. Under normal physiological conditions, HSA has an effect of maintaining plasma colloid osmotic pressure, nourishing, accelerating concrescence of wounds, and as a carrier, participating in transportation of many hydrophobic biological molecules such as hormones, biological active substances and drugs in the blood. Therefore, HSA is an important medical protein that is mainly used clinically for treatment of hypoproteinemia caused by loss of blood, burn, scald, plastic surgery and brain lesion, as well as for treatment of liver cirrhosis, hydronephrosis and so on.

At present, HSA for clinical use is mainly prepared by extraction and isolation from human plasma. However, this preparation approach has the following disadvantages: on one hand, the source of plasma is insufficient, i.e. the limited blood supply is unable to meet the demands of production of HSA and the relevant preparations thereof; on the other hand, blood itself may potentially be a risk factor, for example it may contain dangerous infectious pathogens such as hepatitis virus, human immunodeficiency virus (HIV) and so on, which causes enormously concerns about the application of HSA extracted from plasma. Therefore, it is urgent to develop an alternative process to produce HSA.

With the development of modern DNA recombinant and synthesis techniques, researchers take a profound interest in the production and application of recombinant human serum albumin (rHSA). So far, various expression systems have been experimentally used for mass production rHSA. For example, prokaryotes such as colon bacillus (Latta, M. et al., Bio/Technology, 5:1309-1314, (1987)), bacillus subtilis (Saunders, C. W. et al, J. Bacteriol. 169: 2917-2925, (1987)), eukaryotes such as yeasts (WO 00/44772, EP0683233A2, U.S. Pat. No. 5,612,196) and also cultivation of animal cells have been used for production of rHSA. However, such approaches supra are not suitable for industrialized production either due to low expression level or high production cost.

Chinese patent application No. 200510019084 of the present inventors discloses a method for producing rHSA using rice endosperm cells as bioreactor, comprising: using promoters and signal peptides specifically expressed in rice endosperm to mediate the entry of rHSA into endomembrane system of the endosperm cells of rice and store rHSA in the protein bodies of the rice endosperm, thus allowing rHSA to accumulate extensively in the rice seed and reach a higher expression level finally. The expression level of the obtained rHSA is at least above 0.3% based on the weight of the rice seed. The method has the advantages of high expression level and low cost, thereby it provides the possibility to develop a novel strategy for the production of protein drugs.

At present, there is no mature production process for extracting rHSA from transgenic rice grain. Establishing method and process for extracting proteins from transgenic rice grain, improving the extraction efficiency of target proteins and reducing the extraction yield of non-target proteins are critical elements of the research and technology development. The present invention establishes a technology and process for high-efficiency extraction of rHSA from transgenic rice grain on a large scale.

SUMMARY OF THE INVENTION

The object of the invention is to provide a method for extracting recombinant human serum albumin (rHSA) from transgenic rice grain.

To achieve the above object, the present invention provides the following technical solution:

A method for extracting recombinant human serum albumin from transgenic rice grain, comprising the steps of:
1) removing the hull of transgenic paddy rice containing recombinant human serum albumin, grinding the dehusked rice grain, followed by mixing the transgenic milled rice grain with an extraction buffer and extracting with stirring to obtain mixture I;
2) adjusting pH of the mixture I of step 1) to 4.0~4.5 and precipitating it for 1~12 hours to obtain mixture II;
3) filtrating the mixture II of step 2) and collecting the filtrate to obtain a solution containing high concentration of recombinant human serum albumin.

Specifically, in step 1), as recombinant human serum albumin presents among the starch granules in rice endosperm cells, in order to reduce the extraction yield of non-target proteins, the transgenic rice grain containing rHSA is husked and the husked rice grain is milled into rice powder or ground rice with a fineness of 80~120 mesh in size to enhance the extraction yield of recombinant human serum albumin.

The extraction buffer comprises 10~30 mM phosphate buffer (PBS), 10~20 mM sodium acetate, 10~50 mM ammonium sulfate and 5~40 mM sodium caprylate, and the extraction buffer has a pH of 6.5~8.

In the extraction buffer, said ammonium sulfate preferably has a concentration of 10~30 mM, more preferably 15~30 mM, and most preferably 20~30 mM.

In the extraction buffer, said sodium caprylate preferably has a concentration of 5~30 mM, more preferably 5~20 mM, and most preferably 10~20 mM.

For example, in an embodiment, the extraction buffer comprises 10~30 mM phosphate buffer (PBS), 10~20 mM sodium acetate, 15~30 mM ammonium sulfate and 5~20 mM sodium caprylate; and the extraction buffer has a pH of 6.5~8.

In a preferred embodiment, the extraction buffer comprises 25 mM phosphate buffer, 20 mM sodium acetate, 20 mM ammonium sulfate and 20 mM sodium caprylate, and has a pH of 7.5.

In order to obtain the highest extraction yield of recombinant human serum albumin and balance the relationship between extraction volume and extraction efficiency, the rice powder is mixed with the extraction buffer in a w/v ratio (kg/L, weight of the ground rice/volume of the extraction buffer) from 1:5 to 1:10, then extracted with stirring at 60 rounds per minute (rpm) for 1~3 hours. It is showed by the experiments that the ratio ranging from 1:5 to 1:10 have no obvious influence on the extraction efficiency of the recombinant human serum albumin. For the purpose of reducing cost and extraction volume, the transgenic ground rice are preferably mixed with the extraction buffer in a w/v (kg/L) ratio of 1:5, and the extraction time is preferably 1~1.5 hours.

In order to extract recombinant human serum albumin from the milled rice grain with maximal efficiency, according to the characteristic feature of the human serum albumin being stable at 60° C., an increase of the extraction temperature obviously enhance the extraction yields of total proteins and recombinant human serum albumin provided that the USA is not denatured at the temperature. Therefore, heat treatment is employed in the present invention to effectively increase the extraction yield of the recombinant human serum albumin. Said extraction temperature is 45~60° C., and preferably 55~60° C.

Since both of the extractions of the recombinant human serum albumin and non-target proteins are enhanced under the conditions of heating and high pH, removing the additional non-target proteins of the above-mentioned process could be realized by precipitating reserve proteins of rice endosperm at the isoelectric point of the human serum albumin. The precipitation process in step 2) according to the present invention is performed at low pH. After extracting, the extracted mixture is adjusted to pH 4.0~4.5, then the mixture is precipitated at room temperature for at least 1 hour to eliminate the negative effects of excess non-target proteins produced by extracting process under heating and high pH. In an embodiment, acetic acid is used to adjust the pH to 4.0~4.5, preferably 4.5; the precipitation time is 1~12 hours, preferably 3~12 hours, and more preferably 6 hours.

According to the different physical characteristics between the starch granules existed in ground rice and liquid portion, the routine techniques and equipments may be used to separate undesirable substances from protein extraction. The extracted mixture obtained from the precipitation process in step 2) is subjected to a solid-liquid separation via pressure filtration or other equivalent equipments, achieving the purpose of separating waste starch from the target protein effectively on a large scale. The invention provides a simple, quick and low cost method to obtain a solution containing high concentration of recombinant human serum albumin finally.

In one embodiment, said filtration comprises steps of filtrating by pressure filtration with a filter cloth type plate-frame press filter, followed by filtrating by micro-filtration with a hollow fiber membrane. Said hollow fiber membrane is made of polyethersulfone hollow fiber membrane, having a pore size of 0.20 μm~0.45 μm in diameter, and preferably 0.22 μm.

In the solution containing recombinant human serum albumin prepared according ix the method of the present invention, the concentration of the recombinant human serum albumin is 0.65~0.66 mg/mL; the initial concentration of total proteins is 6.90~7.05 mg/mL and is reduced to about 2.8 mg/mL after the precipitation step; the content of non-target proteins is substantially reduced.

The technical solution of the present invention has the following advantages:

1. The extraction efficiency of recombinant human serum albumin is enhanced by combination of different pH and different salt concentrations. The data showed that the concentration of recombinant human serum albumin in the extract obtained according to the present invention is 0.65~0.66 mg/mL, while the concentration obtained by previous technique is only 0.30~0.315 mg/mL. Thus, applying the improved method of present invention, the extraction amount of recombinant human serum albumin from the same weight of milled rice is increased by 1.15 times.

2. The extraction efficiency of non-target protein is reduced. The concentration of total proteins in the initial extract according to the present invention is 6.90~7.05 mg/mL and the content of total protein is 2.8 mg/mL after precipitation step, which is reduced by 2.46 times.

3. The aseptic effect or sterilization effect is enhanced due to the improvement of microfiltration step, which eliminates microbial contamination that may be introduced into the subsequent purification step and reduces the amount of bacterial endotoxins that may occur in production process.

DETAILED DESCRIPTION OF THE INVENTION

The features and advantages of the present invention can be further understood from folk ring examples. The examples are illustrative only and should not to be construed as limiting the invention in any way.

Example 1: Extraction of rHSA According to the Improved Method of Present Invention Transgenic rice could be prepared according to the method disclosed in Chinese patent application No. 200510019084 of the present inventors. The paddy rice was hulled to obtain half-polished rice and grinded to obtain milled rice with a fineness of 80~100 mesh. The milled rice was mixed with an extraction buffer in a ratio of 1:5 (w/v, kg/L), and extracted for 1.5 hours at 60° C. The components of the extraction buffer are: 25 mM phosphate buffer, 20 mM sodium acetate, 10 mM ammonium sulfate, 10 mM sodium caprylate; pH 7.5. The resultant mixture was adjusted to pH 4.5 with acetic acid and placed for at least 3 hours to precipitate non-target proteins. Then the resultant mixture was sequentially subjected to pressure filtration using a plate-frame press filter (filter cloth type) and micro-filtration by hollow fiber column with a pore size of 0.22 µm, to obtain supernatants containing rHSA. The concentration of rHSA was about 0.66 mg/mL.

Example 2: Extraction of rHSA According to the Previous Method in the Art

Transgenic rice can be prepared according to the method disclosed in Chinese patent application No. 200510019084 of the present inventors. The paddy rice was hulled to obtain unpolished rice and milling to obtain milled rice with a fineness of 80~100 mesh. The ground rice was mixed with an extraction buffer in a ratio of 1:5 (w/v, kg/L) and extracted at least for 1 hour at room temperature. The components of the extraction buffer are: 25 mM phosphate buffer and 20 mM sodium acetate; pH 6.5. The resultant mixture was adjusted to pH 4.5 with acetic acid and placed for 1 hour to produce precipitation.

Then the resultant mixture was sequentially subjected to pressure filtration using a plate-frame type press filter (filter cloth type) and micro-filtration by hollow fiber column with a pore size of 0.45 µm, to obtain supernatants containing rHSA. The concentration of rHSA was about 0.314 mg/mL. Compared to the results according to the improved method of the present invention, the content of total proteins was only 45.5%, and the content of rHSA was 47.7% (FIGS. 1 to 3).

Example 3: Effects of Extraction Temperature and Time on the Extraction Yield of rHSA This example employed a constant extraction buffer and performed orthogonal combination on different temperatures (45° C., 50° C., 55° C., 60° C., respectively) and different extraction times (20 min, 40 min, 60 min, 80 min, respectively) to obtain different extract samples. BCA method was used to determine the concentration of total proteins in each sample and ELISA was used to determine the concentration of rHSA in each sample. The results were shown in FIGS. 1 and 2, respectively. Each sample was subjected to SDS-PAGE and the electrophoresis photograph was shown in FIG. 3.

Figure 1:
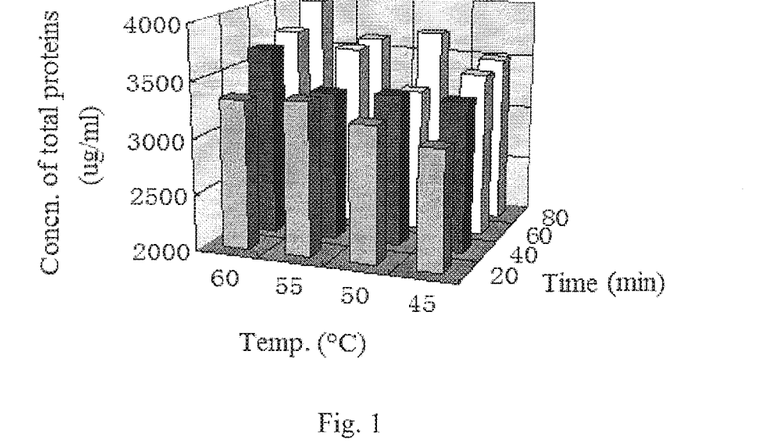
FIG. 1 is a graph showing the effects of combining the different extraction temperatures and times on the extraction yield of total proteins from milled transgenic rice grain.
Figure 2:
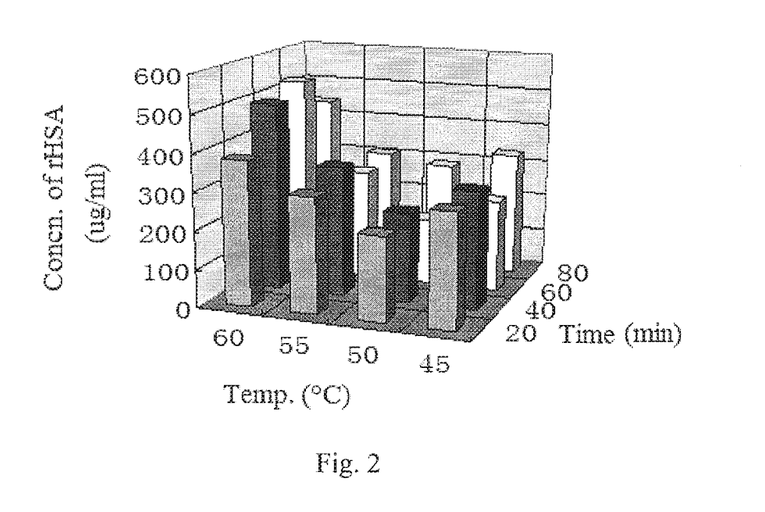
FIG. 2 is a graph showing the effects of combining the different extraction temperatures and times on the extraction yield of rHSA from milled transgenic rice grain.
Figure 3:
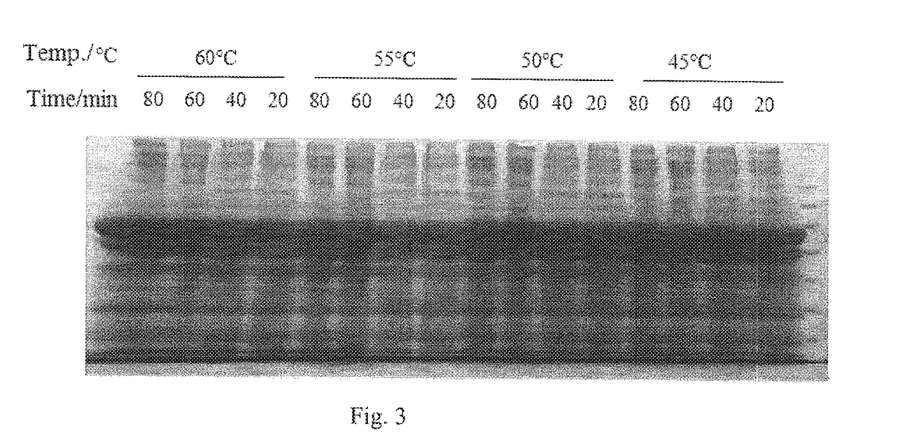
FIG. 3 is an image of SDS-PAGE of samples obtained by orthogonal combinations of different extraction temperatures and times.

It can be seen from FIGS. 1 and 2 that with an increase of extraction time and temperature, the concentrations of total proteins and rHSA in the extract of the ground rice tend to increase correspondingly. The extraction temperature had a larger influence on the extraction efficiency than the extraction time. The highest extraction efficiency of rHSA was obtained when the extraction was performed at 60° C. for 60 mins. It was seen from the electrophoresis photograph in FIG. 3, under different temperature and time conditions, the spectral bands of the extracted proteins had a significant difference at the area where the molecular weight was larger than that of rHSA, while the spectral bands were identical at the area where the molecular weight was lower than that of rHSA at different extraction conditions.

Example 4: Effects of the pH Value of Extraction Buffer and Salt Concentration of Ammonium Sulfate on the Extraction Yield of rHSA This example employed a constant condition to extract at 55° C. for 60 min. The ratio of milled rice to extraction buffer (w/v, kg/L) was 1:5. Orthogonal combinations were performed on different concentrations of ammonia sulfate (0, 10, 30, 50 mM, respectively) and pH of extraction buffer (pH 6.5, 7, 7.5, 8, respectively), BCA method was used to determine the concentration of total proteins and ELISA was used to determine the concentration of rHSA in each sample. The results were shown in FIGS. 4 and 5, respectively. The SDS-PAGE of the samples obtained by orthogonal combinations of different concentrations of ammonia sulfate and pH of extraction buffer was shown in FIG. 6.

Figure 4:
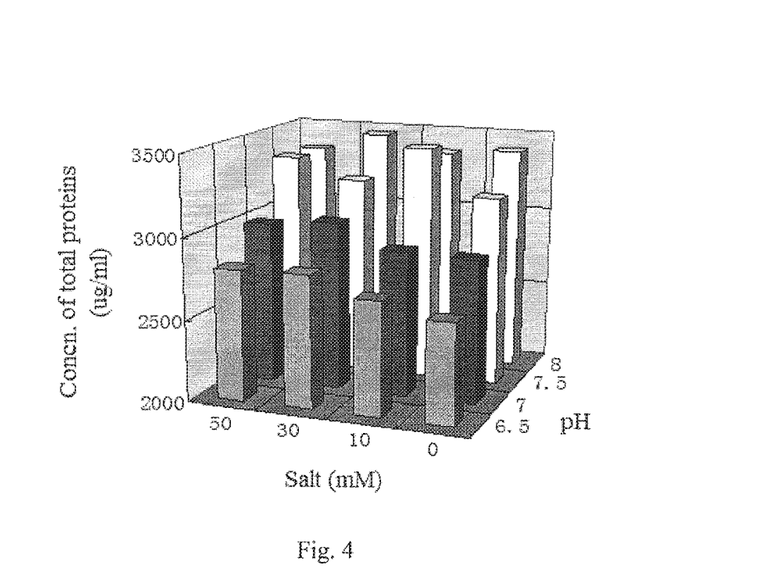
FIG. 4 is a graph showing the effects of combining different pH and salt concentrations of ammonium sulfate on the extraction yield of total proteins from milled transgenic rice grain.
Figure 5:
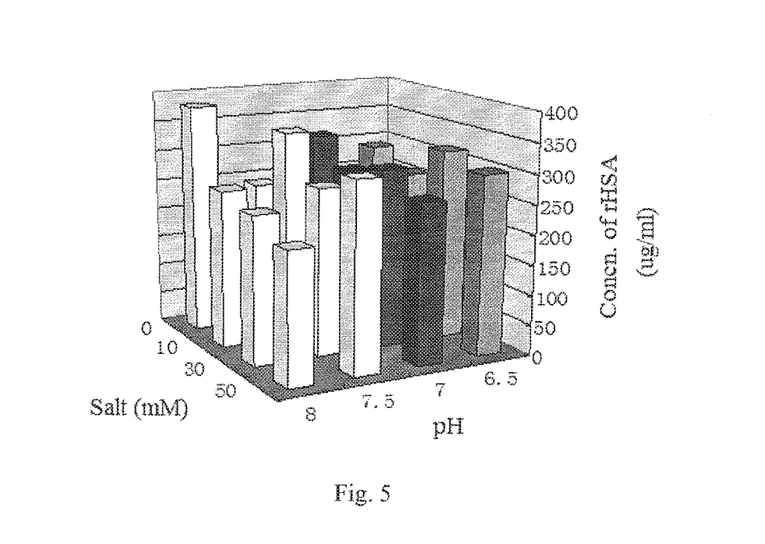
FIG. 5 is a graph showing the effects of combining different pH and salt concentrations of ammonium sulfate on the extraction yield of rHSA from milled transgenic rice grain.
Figure 6:
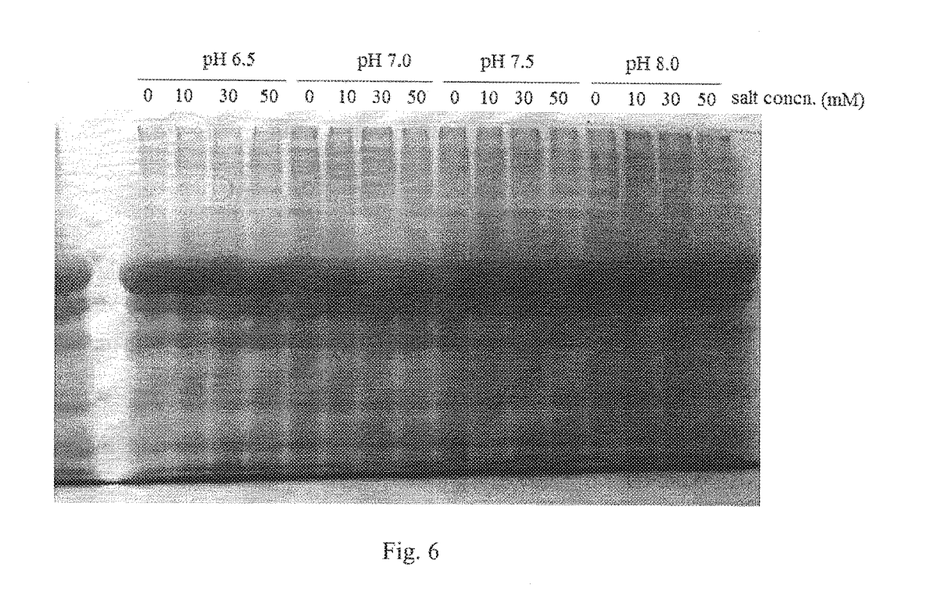
FIG. 6 is an image of SDS-PAGE of samples obtained by orthogonal combinations of different pH and salt concentrations of ammonium sulfate.

It can be seen from the results of FIGS. 4 and 5 that with an increase of pH of the extraction buffer and salt concentration, the concentrations of total proteins and rHSA in the extract of ground rice tended to increase correspondingly, with deviation in individual cases. The pH of the extraction buffer had a significantly larger influence on the extraction yield of rHSA than the salt concentration of the extraction buffer. Under such a condition where the pH of extraction buffer was 7.5 and the salt concentration was 10 mM, the extraction efficiency of rHSA was the highest. Compared to different extraction times and temperatures, different pH and salt concentrations had only a less influence on the bands of extracted proteins. When at a higher pH, there were slightly more small bands above the main band of rHSA, while other main bands retained identical, as shown in FIG. 6.

Example 5: Effects of Precipitation Time and Concentration of Sodium Caprylate on the Extraction Yield of rHSA The concentrations of sodium caprylate were provided as 1.0 mM, 20 mM, 30 mM and 40 mM respectively to test whether an increase of the concentration of sodium caprylate had a better protecting effect on rHSA. After extracting, acetic acid was added to adjust the pH to 4.5, and the resultant mixture was precipitated for 0 h, 1 h, 2 h, 3 h and overnight respectively to determine the concentration of the protein. The effect of different precipitation times and concentrations of sodium caprylate on the extract of total proteins was shown in FIG. 7. The SDS-PAGE pattern of the samples obtained at different concentrations of sodium caprylate and precipitation times was shown in FIG. 8. The extract of FIGS. 7 and 8 referred to the mixture samples after extracting but prior to adjusting pH.

Figure 7:
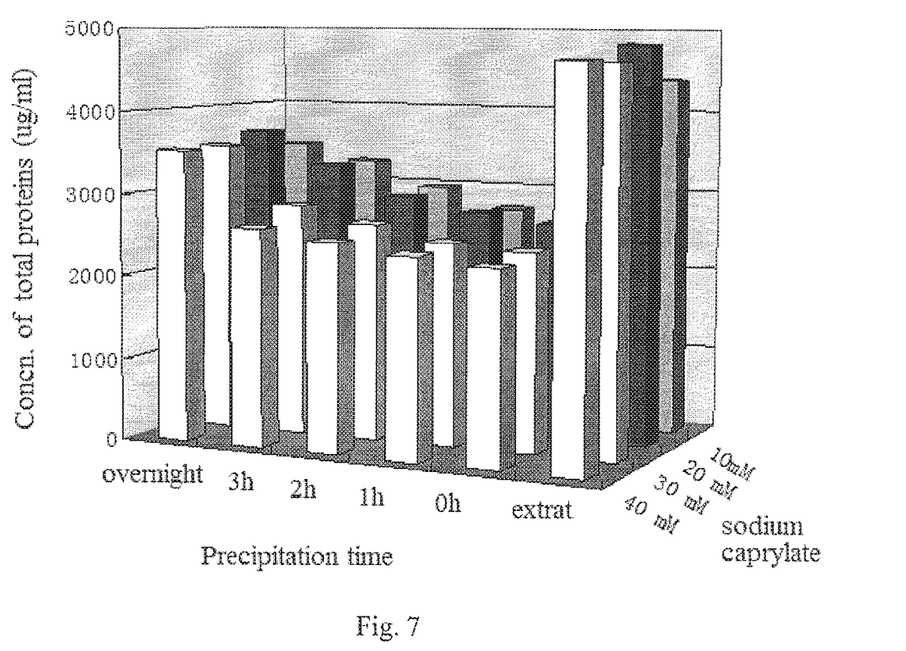
FIG. 7 is a graph showing the effects of different concentrations of sodium caprylate- and precipitation times on the extraction yield of total proteins.
Figure 8:
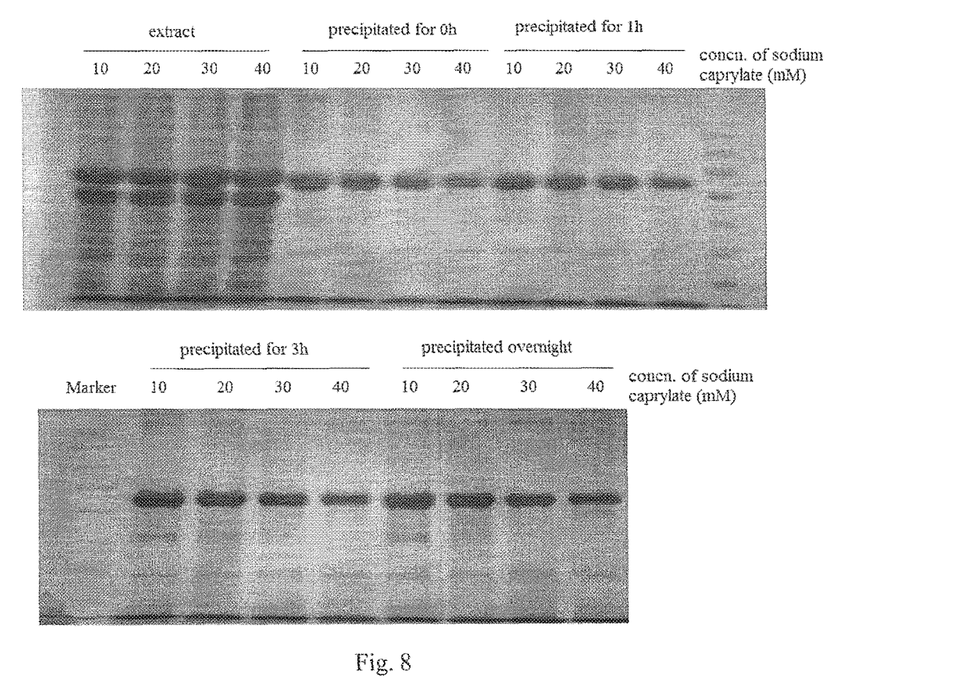
FIG. 8 is an image of SDS-PAGE of the extraction samples obtained at different concentrations of sodium caprylate and precipitation times.

It can be seen from FIGS. 7 and 8 that the shock of adjusting pH of the extraction solution to 4.5 resulted in lots of precipitated rHSA. As the precipitation time increases, a portion of precipitated rHSA re-dissolved. After precipitating overnight, the average concentration of total proteins was 78% based on the value before precipitating and there was no degradation phenomenon after precipitating overnight. Meanwhile degraded bands and non-target proteins were also largely precipitated during the precipitation process. It was shown that 20 mM of sodium caprylate had the best protecting effect, while higher concentration causes increased precipitation.

Example 6: Effects of pH and Time on Precipitation Efficiency

In order to determine the effect of pH and precipitation time on the precipitation efficiency, the ground rice was mixed with a extraction buffer (25 mM of phosphate buffer, 10 mM of ammonium sulfate, 10 mM of sodium caprylate, pH 7.5) in a ratio (w/v, kg/L) of 1:5, then extracted at 60° C. for 1 hour with stirring. The resultant extract of the milled rice grain was divided into six equal parts, which were adjusted to pH 4.5, 4.4, 4.3, 4.2, 4.1, 4.0, respectively. The pH-adjusted extracts were shook on a shaking bed at room temperature for 1 and 2 hours respectively, followed by sampling. The SDS-PAGE pattern of the samples was shown in FIG. 9. The extract of FIG. 9 referred to the mixture sample after extracting, but prior to adjusting pH.

Figure 9:
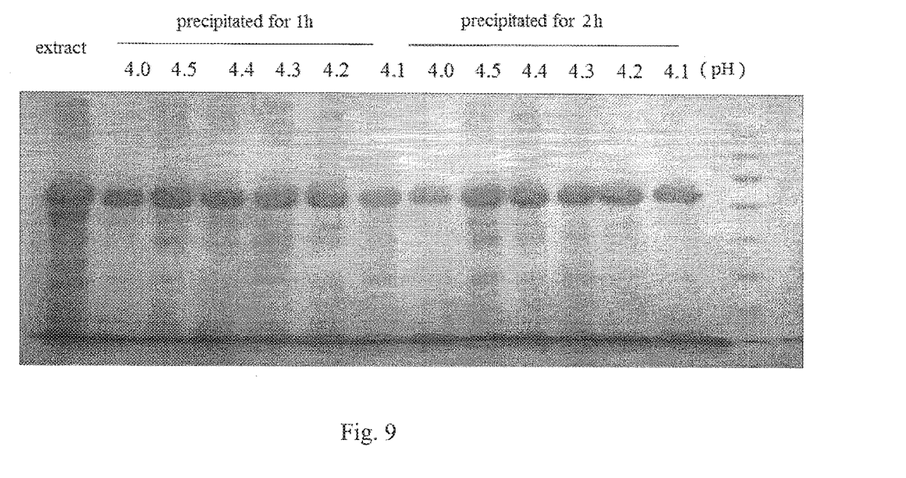
FIG. 9 is an image of SDS-PAGE of the extraction samples obtained at different pH and precipitation times.

It can be seen from the SDS-PAGE pattern of FIG. 9 that as the pH decreased, the precipitation efficiency of non-target proteins was enhanced, together with the loss of rHSA. The extension of precipitation time has a positive effect on the precipitation efficiency. At a pH below 4.1, macromolecular bands were precipitated completely. Considering the technical requirements of the process system and minimizing the loss of target rHSA, precipitating at pH 4.5 is preferable.

Example 7: Comparison Between Sterilization Effects Using Different Sizes of Polyethersulfone (PES) Hollow Fiber Membrane in Micro-Filtration Step 1. Effect of Micro-Filtration with Different Filter Membranes on Removing Bacteria in the Rice The solution samples used in this example were clear filtrate from pressure filtration, which was obtained by treatment of transgenic ground rice using the improved process according to the present invention in pilot scale production. The samples were treated by small hollow fiber columns with a pore size of 0.20 μm and 0.45 μm respectively. Both the original solution before treatment and the filtrate after the treatment were collected. 0.1 ml of the original solution or its dilution solutions were respectively applied on LB plates to review the sterilization effect of the two filter membranes. The results were shown in Table 1. The concentrations of recombinant human serum albumin and total proteins in the solutions before or after filtrating were determined, and the percentages of recombinant human serum albumin in total proteins were calculated. The percentage bar graph was shown in FIG. 10.

TABLE 1

| Dilution degree | 1.0 | $10^{-1}$ | $10^{-2}$ | $10^{-3}$ | $10^{-4}$ | $10^{-5}$ | CFU |
|---|---|---|---|---|---|---|---|
| Sample after pressure filtration | 382 | 37 | 2 | 2 | 0 | 1 | 3800 |
| Sample after 0.45 μm filtration | 41 | 7 | 0 | 0 | 0 | 0 | 400-700 |
| Sample after 0.20 μm filtration | 0 | 0 | 0 | 0 | 0 | 0 | 0 |

It can be seen from the results of table 1 that 0.45 μm hollow fiber membrane can remove 50%~90% of living bacteria in the filtrate from pressure filtration, in contrast 0.20 μm hollow fiber membrane can remove 100% of living bacteria in the filtrate from pressure filtration, ensuring that microbial contamination could not be introduced into the subsequent purification step through the filtrate, thereby reducing the content of bacterial endotoxins in the production process.

Figure 10:
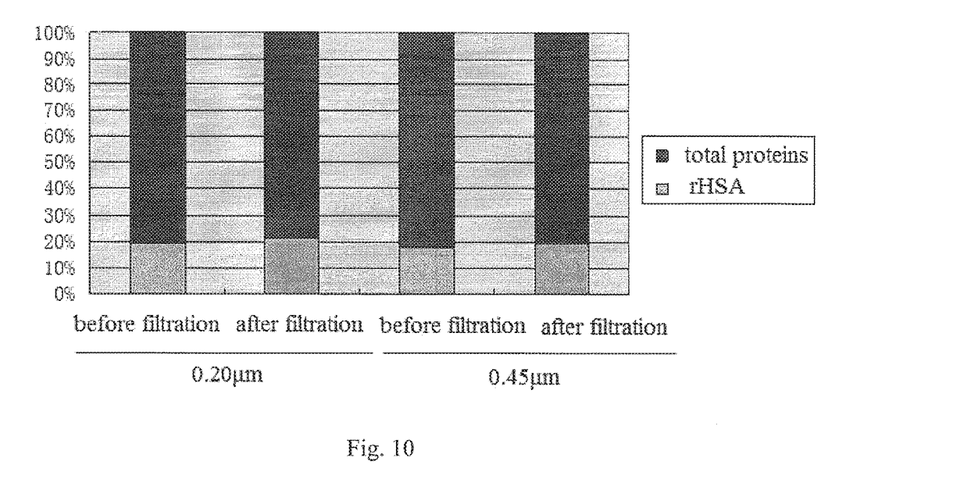
FIG. 10 is a schema showing the percentages of rHSA in total proteins of the extracted solution prior to and after filtrating with different pore size of membranes.

With respect to FIG. 10, comparing with the filtrated samples of 0.20 μm and 0.45 μm hollow fiber membrane, when filtrated with 0.20 μm membrane, the loss of recombinant human serum albumin is much less than that of total proteins. The extract that was filtrated with 0.20 μm membrane had a relatively higher concentration of recombinant human serum albumin.

What is claimed is:

1. A method for extracting recombinant human serum albumin from transgenic rice grain, comprising the steps of:
   1) removing the hull of transgenic paddy rice containing recombinant human serum albumin, and grinding the dehusked rice grain;
   2) mixing the transgenic milled rice grain with an extraction buffer and extracting with stirring to obtain mixture I,
   wherein the extraction buffer has a pH of between about 6.5 and about 8, and comprises between about 10 mM and about 30 mM phosphate, between about 10 mM and about 20 mM sodium acetate, between about 10 mM and about 50 mM ammonium sulfate, and between about 5 mM and about 40 mM sodium caprylate;
   3) adjusting pH of the mixture I of step 2) to between about 4.0 and about 4.5 and precipitating non-target proteins for between about 1 hour and about 12 hours to obtain mixture II; and
   4) filtrating the mixture II of step 3) and collecting the filtrate to obtain a solution containing high concentration of recombinant human serum albumin.

2. The method of claim 1, wherein step 1) comprises grinding the dehusked rice grain to a fineness of between about 80 mesh and about 120 mesh.

3. The method of claim 1, wherein step 2) comprises extracting for between about 1 hour and about 3 hours.

4. The method of claim 1, wherein step 2) comprises extracting at a temperature of between about 45° C. and about 60° C.

5. The method of claim 1, wherein in step 2), the transgenic milled rice grain and the extraction buffer are mixed in a w/v (kg/L) ratio ranging from about 1:5 to about 1:10.

6. The method of claim 1, wherein the filtrating step is accomplished by pressure filtration with a filter cloth type plate-frame press filter followed by micro-filtration with a polyethersulfone hollow fiber membrane.

7. The method of claim 6, wherein said polyethersulfone hollow fiber membrane has a pore size of between about 0.20 μm and about 0.45 μm.

8. The method of claim 7, wherein said polyethersulfone hollow fiber membrane has a pore size of about 0.22 μm.

9. The method of claim 1, wherein the extraction buffer comprises between about 10 mM and about 30 mM ammonium sulfate.

10. The method of claim 1, wherein the extraction buffer comprises between about 5 mM and about 30 mM sodium caprylate.

11. The method of claim 1, wherein the extraction buffer comprises between about 15 mM and about 30 mM ammonium sulfate.

12. The method of claim 1, wherein the extraction buffer comprises between about 5 mM and about 20 mM sodium caprylate.

13. The method of claim 1, wherein the extraction buffer has a pH of between about 7.0 and about 7.5.

14. The method of claim 1, wherein the extraction buffer comprises about 25 mM phosphate, about 20 mM sodium acetate, about 20 mM ammonium sulfate, and about 20 mM sodium caprylate.

15. The method of claim 14, wherein the extraction buffer has a pH of about 7.5.

16. The method of claim 1, wherein in step 2) said transgenic milled rice grain and said extraction buffer are mixed in a w/v (kg/L) ratio of about 1:5, the extraction time is between about 1 hour and about 1.5 hours, and the extraction temperature is between about 55° C. and about 60° C.

17. The method of claim 1, wherein in step 3) said mixture I is adjusted to pH 4.0-4.5 and then precipitated for 3-12 hours at room temperature.

18. The method of claim 17, wherein in step 3) said mixture I is adjusted to pH 4.5 and precipitated for 6 hours.

19. The method of claim 1, wherein the filtrating step removes between about 50% and about 90% of living bacteria in the filtrate.

20. The method of claim 1, wherein the filtrating step removes 100% of living bacteria in the filtrate.

* * * * *